(12) United States Patent
Erickson et al.

(10) Patent No.: US 10,316,347 B2
(45) Date of Patent: Jun. 11, 2019

(54) ENDOSPORE DETECTION USING HYDROPHOBIC COLLECTION MATERIAL

(71) Applicant: Ecolab USA Inc., Saint Paul, MN (US)

(72) Inventors: Anthony Wayne Erickson, Golden Valley, MN (US); Elaine Patricia Black, St. Paul, MN (US); Nathan Richard Ortmann, Buffalo, MN (US); Rodney H. Banks, Aurora, IL (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

(21) Appl. No.: 14/315,606

(22) Filed: Jun. 26, 2014

(65) Prior Publication Data

US 2015/0376675 A1     Dec. 31, 2015

(51) Int. Cl.
*C12Q 1/06* (2006.01)
*C12Q 1/24* (2006.01)

(52) U.S. Cl.
CPC .............. *C12Q 1/06* (2013.01); *C12Q 1/24* (2013.01)

(58) Field of Classification Search
CPC ... C12Q 1/06; C12Q 1/24; C12Q 1/22; G01N 2333/195
USPC ................................. 435/7.32, 31
See application file for complete search history.

(56) References Cited

U.S. PATENT DOCUMENTS

| | | | |
|---|---|---|---|
| 4,021,306 A | 5/1977 | Soper, Jr. | |
| 5,124,268 A | 6/1992 | Dakubu | |
| 5,701,012 A | 12/1997 | Ho | |
| 5,876,960 A | 3/1999 | Rosen | |
| 5,895,922 A | 4/1999 | Ho | |
| 6,596,496 B1 | 7/2003 | Rotman | |
| 6,599,715 B1 | 7/2003 | Vanderberg et al. | |
| 6,750,006 B2 | 6/2004 | Powers et al. | |
| 6,815,178 B1 | 11/2004 | Shoaf | |
| 6,838,292 B1 | 1/2005 | Rajan et al. | |
| 6,872,539 B2 | 3/2005 | Rotman | |
| 6,885,440 B2 | 4/2005 | Silcott et al. | |
| 7,064,241 B2 | 6/2006 | Brown et al. | |
| 7,183,048 B2 | 2/2007 | Felkner et al. | |
| 7,211,377 B1 | 5/2007 | Powers et al. | |
| 7,306,930 B2 | 12/2007 | Ponce et al. | |
| 7,312,071 B2 | 12/2007 | Lu et al. | |
| 7,343,782 B2 | 3/2008 | Damer et al. | |
| 7,485,437 B1 | 2/2009 | Rosen et al. | |
| 7,563,615 B2 | 7/2009 | Ponce | |
| 7,608,419 B2 | 10/2009 | Ponce | |
| 7,611,862 B2 | 11/2009 | Ponce | |
| 7,622,723 B2 | 11/2009 | Reinisch et al. | |
| 7,713,914 B2 | 5/2010 | Farquharson et al. | |
| 7,718,421 B2 | 5/2010 | Chen et al. | |
| 7,923,242 B2 | 4/2011 | Kono et al. | |
| 8,159,661 B2 | 4/2012 | Moshe et al. | |
| 8,173,359 B2 | 5/2012 | Ponce et al. | |
| 8,685,746 B2 | 4/2014 | Halverson et al. | |
| 8,711,354 B2 | 4/2014 | Reinisch et al. | |
| 8,817,253 B2 | 8/2014 | Moshe et al. | |
| 8,846,327 B2 | 9/2014 | Fujinaka et al. | |
| 8,936,933 B2 | 1/2015 | Chen et al. | |
| 2005/0221418 A1 | 10/2005 | Fell, Jr. et al. | |
| 2006/0257891 A1 | 11/2006 | Farquharson et al. | |
| 2006/0292664 A1 | 12/2006 | Ponce | |
| 2010/0108911 A1 | 5/2010 | Reinisch et al. | |
| 2012/0164681 A1 | 6/2012 | Reinisch | |
| 2013/0045502 A1 | 2/2013 | Reinisch | |
| 2014/0073001 A1 | 3/2014 | Reinisch | |
| 2015/0004683 A1 | 1/2015 | Ponce et al. | |

FOREIGN PATENT DOCUMENTS

| | | |
|---|---|---|
| EP | 0566010 A1 | 10/1993 |
| WO | 03052127 A1 | 6/2003 |
| WO | 2007030020 A1 | 3/2007 |
| WO | 2008122975 A2 | 10/2008 |

OTHER PUBLICATIONS

Carrera et al. Difference Between the Spores Sizes of Bacillus Anthracis and Other *Bacillus* Species; Journal of Applied Microbiology, vol. 102 (2007) pp. 303-312.*
Tate et al. Interferences in Immunoassay; Clinical Biochemist Reviews, vol. 25 (2004) pp. 105-120.*
Nudelman et al. Fluorescence Emission Derived From Dipicolinic Acid, Its Sodium, and Its Calcium Salts; Applied Spectroscopy, vol. 54, No. 3 (2000) pp. 445-449.*
Baker et al., "Bacterial Bioluminescence: Applications in Food Microbiology," Abstract, Journal of Food Protection, 1991, vol. 55, No. 1, pp. 62-70, abstract only.
Blake et al., "Immunomagnetic Detection of Bacillus Stearothermophilus Spores in Food and Environmental Samples," Abstract, Applied and Environmental Microbiology, 1997, vol. 63, No. 5, pp. 1643-1646, abstract only.
Blake, "Microbiological and Sensory Effects of Processing Milk for Extended Shelf Life and the Development of Rapid Methods to Quantitate Spores and Lipase Activity," Abstract, Disseration Abstracts International, B, 1996, vol. 58, No. 6, 117 pages, abstract only.

(Continued)

*Primary Examiner* — Paul C Martin
(74) *Attorney, Agent, or Firm* — Fredrikson & Byron, P.A.

(57) ABSTRACT

In situ optical analysis of bacterial endospores can be inhibited when the endospores are present within an optically active carrier medium. To help isolate the endospores from the carrier medium, in some examples, the carrier medium is passed through a hydrophobic material that captures the endospores via hydrophobic attraction. Subsequently, a germination fluid and lanthanide source, such as terbium, can be added to the bacterial endospores captured on the hydrophobic material to form a lanthanide-dipicolinic acid complex in the germination fluid. The germination fluid can then be optically analyzed by measuring the fluorometric response of the lanthanide-dipicolinic acid complex to determine a concentration of the bacterial endospores in the carrier medium.

31 Claims, 6 Drawing Sheets

(56) References Cited

OTHER PUBLICATIONS

Cable et al., "Bacterial Spore Detection by [Tb3+(macrocycle)(dipicolinate)] Luminescence," Journal of the American Chemical Society, Feb. 14, 2007, vol. 129, No. 6, pp. 1474-1475.

Cable et al., "Detection of Bacterial Spores with Lanthanide-Macrocycle Binary Complexes," Journal of the American Chemical Society, Jul. 15, 2009, vol. 131, No. 27, pp. 9562-9570.

Dostalek et al., "Prospects for Rapid Bioluminescent Detection Methods in the Food Industry—A Review," Abstract, Czech Journal of Food Sciences, 2005, vol. 23, No. 3, pp. 85-92, abstract only.

Goepfert et al., "One-Day Fluorescent-Antibody Procedure for Detecting Salmonellae in Frozen and Dried Foods," Abstract, Applied Microbiology, 1970, vol. 20, No. 6, pp. 977-983, abstract only.

Jobstl et al., "Clostridium Difficile in Raw Products of Animal Origin," Abstract, International Journal of Food Microbiology, 2010, vol. 138, No. 1-2, pp. 172-175, abstract only.

Kelly et al., "Use of the Direct Epifluorescent Filter Technique for the Enumeration of Bacterial Spores," Abstract, Journal of Applied Bacteriology, 1987, vol. 63, No. 6, pp. 545-550, abstract only.

LaFlamme et al., "Rapid Detection of Germinating Bacillus Cereus Cells Using Fluorescent In Situ Hybridization," Abstract, Jouranl of Rapid Methods of Automation in Microbiology, 2009, vol. 17, No. 1, pp. 80-102, abstract only.

LaVilla et al., "Detection of Clostridium Tyrobutyricum Spores Using Polyclonal Antibodies and Flow Cytometry," Abstract, Journal of Applied Microbiology, 2010, vol. 108, No. 2, pp. 488-498, abstract only.

Perdue et al., "Detection and Fate of Bacillus Anthracis (Sterne) Vegetative Cells and Spores Added to Bulk Tank Milk," Abstract, Journal of Food Protection, 2003, vol. 66, No. 12, pp. 2349-2354, abstract only.

Sarasanandarajah, "Multiwavelength fluorescence studies of Bacillus bacterial spores," Doctoral Thesis, University of Canterbury, Christchurch, New Zealand, 2007, 200 pages.

White, "Testing of Milk and Milk Products," Abstract, Applied Dairy Microbiology, 2nd Edition, 2002, Chapter 17, pp. 645-680, abstract only.

Yung et al., "Fast Sterility Assessment by Germinable-Endospore Biodosimetry," Applied and Environmental Microbiology, Dec. 2008, vol. 74, No. 24, pp. 7669-7674.

International Search Report & Written Opinion dated Sep. 25, 2015 in PCT Application No. PCT/US2015/038005, 16 pgs.

Seale, et al., "Recovery of spores from thermophilic dairy bacilli and effects of their surface characteristics on attachment to different surfaces," Applied and Environmental Microbiology, 2003, vol. 74, No. 3, pp. 731-737.

Shafaat, et al., "Applications of a rapid endospore viability assay for monitoring UV inactivation and characterizing arctic ice cores," Applied and Environmental Microbiology, 2006, vol. 72, No. 10, pp. 6808-6814.

Valentine, et al., "Evaluation of sampling tools for environmental sampling of bacterial endospores from porous and nonporous surfaces," Journal of Applied Microbiology, 2008, vol. 105, Issue 4, pp. 1107-1113.

European Patent Application No. 15812827, Extended European Search Report dated Nov. 27, 2017, 7 pages.

Rosen et al., "Bacterial Spore Detection and Determination by Use of Terbium Dipicolinate Photoluminescence," Anal. Chem., vol. 69, No. 6, Mar. 15, 1997, pp. 1082-1085, Abstract Only.

\* cited by examiner

```
PASS FLUID ACROSS
HYDROPHOBIC         ~10
MATERIAL
      │
      ▼
FLUSH CAPTURED
BACTERIAL           ~12
ENDOSPORES
      │
      ▼
RELEASE DPA FROM
CAPTURED            ~14
ENDOSPORES
      │
      ▼
ADD LANTHANIDE      ~16
SOURCE
      │
      ▼
OPTICALLY ANALYZE   ~18
```

ENDOSPORE DETECTION USING HYDROPHOBIC COLLECTION MATERIAL

TECHNICAL FIELD

This disclosure relates to bacterial endospore isolation and analysis.

BACKGROUND

Bacterial spores are generally accepted to be indicator species for validating sterility since they are the most resilient form of life against sterilization regimens. Traditional bacterial spore analysis is a labor intensive and time consuming process. For example, spore analysis may involve heat activation, serial dilution, plating on a suitable growth medium, and incubation for two to three days until enumeration can be performed. This analysis process can take several days, requiring manufacturers of product undergoing analysis to hold significant quantities of the product before receiving sterility test results that allow them to release product to the marketplace. Moreover, in instances where there is a sterility issue, the lack of real-time information can result in several days' worth of production being deemed out of specification and needing to be discarded or repurposed.

In an attempt to provide faster analysis, designers have utilized optical analysis techniques that detect optical emission signals associated with bacterial spores and then correlate these signals with spore count. These techniques are of limited use, however, for many categories of materials desirably analyzed for bacterial spore count. For example, materials that contain a low number of bacterial spores or contain bacterial spores within a surrounding fluid that optically interferes with the emissions associated with the spores can be difficult to evaluate using optical analysis techniques. As one example, dairy production facilities monitoring bacterial spore counts in their products typically cannot use optical emission analysis techniques. This is because proteins and other molecules within the dairy products can optically interfere with emissions produced by bacterial spores.

SUMMARY

In general, this disclosure relates to techniques and systems for analyzing bacterial endospores within fluids. Depending on the application, a fluid containing the bacterial endospores may or may not be optically active such that the fluid surrounding the endospores optically interferes with optical emissions corresponding to the endospores. In either case, the fluid may be passed through a hydrophobic sieve to help isolate the endospores from the surrounding fluid. The hydrophobic sieve may be fabricated from a hydrophobic material and have a porous structure allowing substantially all of the fluid to pass through the hydrophobic sieve. As the endospores contained within the fluid come into proximity of the hydrophobic material while the fluid is passing through the sieve, the endospores may adhere to the surface of the hydrophobic sieve via hydrophobic attraction forces. The fluid surrounding the endospores may continue passing through the hydrophobic sieve. In this manner, the bacterial endospores can be substantially isolated from the carrier fluid.

Once isolated from the surrounding carrier fluid, the bacterial endospores captured on the surface of the hydrophobic sieve via hydrophobic attraction forces can be processed to qualitatively and/or quantitatively evaluate the characteristics of the endospores within the fluid. In some examples, the hydrophobic sieve is flushed with an optically inert flushing fluid such as water to remove residual carrier fluid from the bacterial endospores. In addition or alternatively, a germination fluid may be added to the hydrophobic sieve to germinate the captured bacterial endospores and release dipicolinic acid (DPA) from the core of the spores. When a lanthanide ion source is added to the germination fluid, the lanthanide ion can bind with the DPA to form a lanthanide-DPA complex that fluoresces when optically excited. This fluorescence can be detected and correlated to the concentration of bacterial endospores captured by the hydrophobic sieve which, in turn, can be correlated to the concentration of bacterial endospores in the original carrier fluid.

Using a hydrophobic material, such as a hydrophobic sieve, to help isolate bacterial endospores from a surrounding fluid can be useful for a variety of reasons. In instances where the surrounding fluid is optically active, the hydrophobic material can help separate the bacterial endospores from the optically active fluid. This can remove a source of optical emissions that may otherwise interfere with the emissions produced by the lanthanide-DPA complex during optical analysis of the bacterial endospores. As another example, the hydrophobic material can be used to increase the concentration of bacterial endospores available for analysis, which may increase the range of bacterial endospore concentrations that can be analyzed and/or reduce error effects associated with low endospore concentration fluids. For example, the number of endospores captured by the hydrophobic material may be proportional to the volume of fluid passed across the material. In such applications, the concentration of bacterial endospores available for analysis can be increased by increasing the volume of carrier fluid passed over the hydrophobic material. The concentration of bacterial endospores available for subsequent optical analysis can then be controlled by controlling the amount of germination fluid added to the hydrophobic material. Where the volume of germination fluid added to the hydrophobic material is less than the volume of carrier fluid passed across the material, the concentration of bacterial endospores may be increased for subsequent optical analysis as compared to the concentration in the original carrier fluid. This can be helpful when analyzing fluids having comparatively low concentrations of bacterial endospores.

In one example a method is described that includes passing a fluid containing bacterial endospores across a hydrophobic collection material and thereby collecting bacterial endospores on the hydrophobic collection material. The method also includes releasing dipicolinic acid (DPA) from the collected bacterial endospores and adding a lanthanide source to the dipicolinic acid released from the collected bacterial endospores to form a lanthanide-dipicolinic acid complex. The method further includes determining a concentration of the bacterial endospores in the fluid based on an optical response of the lanthanide-dipicolinic acid complex.

In another example a system is described that includes an aqueous liquid to be evaluated, a germination fluid, a lanthanide source, a hydrophobic collection material, and an optical sensor. The hydrophobic collection material is configured to receive the aqueous liquid and capture therefrom bacterial endospores, receive the germination fluid so as to release dipicolinic acid (DPA) from the captured bacterial endospores, and receive the lanthanide source so as to form a lanthanide-dipicolinic acid complex in the germination fluid. The optical sensor is configured to emit optical energy into the germination fluid and thereby generate optical emissions from the lanthanide-dipicolinic acid complex, detect the optical emissions emitted by the lanthanide-dipicolinic acid complex, and determine therefrom a concentration of bacterial endospores in the aqueous liquid.

In another example a method is described that includes passing an aqueous liquid through a hydrophobic sieve and thereby capturing bacterial endospores present in the aqueous liquid on a surface of the hydrophobic sieve via hydrophobic attraction between the hydrophobic sieve and the bacterial endospores. The method includes adding a germination fluid to the hydrophobic sieve so as to release dipicolinic acid (DPA) from bacterial endospores captured on the hydrophobic sieve and providing a lanthanide source to form a lanthanide-dipicolinic acid complex in the germination fluid with the dipicolinic acid released from the bacterial endospores captured on the hydrophobic sieve. The method further includes fluorometrically analyzing the germination fluid to determine a concentration of bacterial endospores in the aqueous liquid.

The details of one or more examples are set forth in the accompanying drawings and the description below. Other features, objects, and advantages will be apparent from the description and drawings, and from the claims.

DETAILED DESCRIPTION

This disclosure generally relates to the isolation, concentration, and analysis of bacterial endospores from fluids in which the endospores are carried. In some examples, the bacterial endospores are contained within an optically active fluid that emits optical emissions within wavelengths overlapping with the wavelengths at which a lanthanide-dipicolinic acid complex liberated from the bacterial endospores emits. This can prevent direct in-situ optical analysis of the bacterial endospores within the carrier fluid because of optical interference. In some examples in accordance with the disclosure, the carrier fluid is passed across a hydrophobic collection material to help separate the bacterial endospores from the remaining carrier fluid. The hydrophobic collection material can be a porous sieve that the carrier fluid flows through, a sheet of hydrophobic material that is positioned in contact with the carrier fluid, or yet another structure that attracts and holds the bacterial endospores, e.g., via hydrophobic attraction forces. Regardless of the configuration, the hydrophobic collection material can capture and collect bacterial endospores out of the carrier fluid.

Bacterial endospores collected out of the surrounding carrier fluid can be analyzed using a variety of different techniques. In some examples, a germination fluid is added to the hydrophobic collection material to germinate the collected bacterial endospores and release dipicolinic acid (DPA) from the endospores. A lanthanide ion reagent can be added to the germination fluid to form a lanthanide-dipicolinic acid complex. When irradiated with light of appropriate wavelengths, this lanthanide-dipicolinic acid complex may emit fluorescent light that can be detected and quantified. The magnitude and/or wavelength of light emitted by the lanthanide-dipicolinic acid complex corresponds to the concentration of the lanthanide-dipicolinic acid complex in the germination fluid which, in turn, corresponds to the concentration of bacterial endospores in the carrier fluid.

The disclosed systems and techniques for isolating, concentrating, and/or analyzing bacterial endospores can be utilized with any desired fluids that may contain bacterial endospores. Example industries that may use the systems and techniques include the food industry, the beverage industry, the pharmaceutical industry, the chemical industry, the healthcare industry, the water purification industry, and other industries where material is inspected for bacterial endospores. In the case of the food and beverage industry, fluids that may be analyzed for bacterial endospores include those obtained from mammalian-consumable (e.g., human-consumable) food and beverages such as, but not limited to, dairy products (e.g., raw milk, whole and skimmed milk, condensed milk, cream, whey and whey derivatives, buttermilk), juices (e.g., fruit juices such as orange and other citrus juices, apple juice and other pomaceous juices, red berry juice, coconut milk, and tropical fruit juices, vegetable juices such as tomato juice, beetroot juice, carrot juice, and grass juice), and canned foods (e.g., canned fruits, canned vegetables, canned meat). Types of bacteria that may produce endospores desired to be analyzed include, but are not limited to, *Bacillus subtilis, Bacillus cereus, Bacillus amyloliquefaciens, Bacillus atrophaeus, Bacillus megaterium, Bacillus coagulans, Bacillus pumilus, Bacillus mycoides, Bacillus licheniformis, Bacillus sporothermodurans, Bacillus thuringensis, Bacillus weihenstephanensis, Geobacillus stearothermophilus, Clostridium tyrobutyricum, Alicyclobacillus, Clostridium botulinum, Clostridium difficile*, and *Bacillus anthracis*.

In general, the fluid containing bacterial endospores for analysis will be a liquid, such as an aqueous liquid (e.g., water-based liquid), although gaseous carrier fluids containing bacterial endospores can also be evaluated using the systems and techniques. The fluid may be obtained directly from a product sample under analysis or may be formed by combining the product sample with a carrier fluid to extract bacterial endospores from the sample. For example, in instances where the product sample potentially containing bacterial endospores is a solid, the solid may be ground or mixed with a carrier fluid to extract the bacterial endospores for analysis.

The term bacterial endospore generally refers to an endospore produced within a bacterium. The term endospore does not include conidio spores and ascospores of fungi. Endospores typically are non-reproductive structures whose primary function is to ensure survival of the bacterium through periods of environmental stress. Endospores can tolerate extreme drought, heat, and starvation. They are protected by a hardened shell of protein and carbohydrates and produced by a form of binary fission in bacteria. An endospore can comprise the DNA of its parent bacterium, ribosomes, and large amounts of dipicolinic acid. For example, dipicolinic acid may compose greater than 5 weight percent of an endospore's dry weight, such as at least 10 weight percent or at least 15 weight percent, such as from 5 weight percent to 20 weight percent, or from 7 weight percent to 16 weight percent. Dipicolinic acid is a chemical that is believed to help endospores maintain their dormancy.

Because endospores can survive harsh environments and are resilient to sterilization regimes, endospores can be a good indicator species for validating the sterility of a product. The absence of endospores within a product sample and/or the detection of low levels of endospores within the product can indicate that the product is suitably sterile for market release. While such information is useful for a variety of products, the information may be especially valuable for consumable products, such as ingestible foods and beverages. Indeed, governmental regulatory regimes may mandate compliance with certain sterility standards before a product can be sold to the public. The ability to measure endospore count within a product in substantially real-time in accordance with some examples of the present disclosure can enable manufacturers to monitor the quality of their products in substantially real-time and rapidly respond if a sterility issue is detected.

Figure 1:
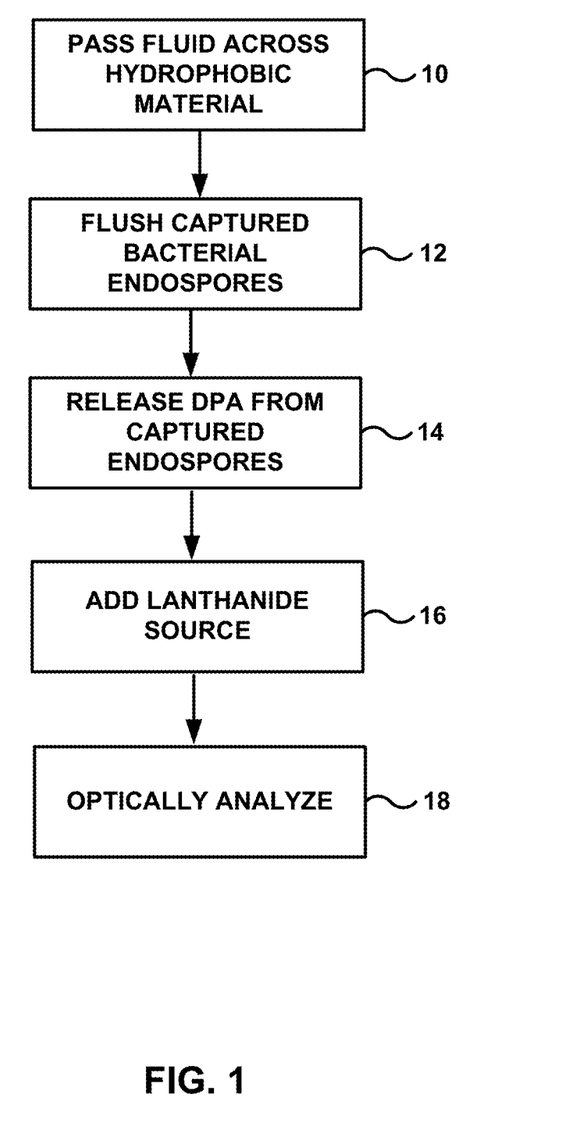
FIG. 1 is a flow diagram illustrating an example process for capturing and analyzing bacterial endospores from a fluid under evaluation.

FIG. 1 is a flow diagram illustrating an example process for capturing and analyzing bacterial endospores from a fluid under evaluation. The process includes passing a fluid to be evaluated across a hydrophobic material (10) to collect bacterial endospores from the fluid, for example, by capturing the endospores on the surface of the hydrophobic material via hydrophobic attraction forces. After capturing the bacterial endospores from the fluid, the bacterial endospores are optionally flushed (12) to remove optically interfering carrier fluid and then processed to release dipicolinic acid (14). In addition, a lanthanide ion source is added to the dipicolinic acid (16) to form a lanthanide-dipicolinic complex that can then be optically analyzed (18) to determine the concentration of the bacterial endospores in the fluid under evaluation. As described in greater detail below, a variety of different processing parameters and conditions can be used to capture and analyze bacterial endospores utilizing the example process of FIG. 1.

To concentrate and/or isolate bacterial endospores from a fluid under evaluation the fluid may be passed over a hydrophobic material (10). Example hydrophobic materials that can be used to concentrate and/or isolate endospores are described in greater detail with respect to FIG. 2. In general, however, the hydrophobic material may be a material or combination of materials chosen to selectively bind with endospores in the fluid under analysis while allowing the surrounding fluid carrying the endospores to pass across the hydrophobic material without binding. When so configured, endospores present in the fluid under analysis may attach to the surface of the hydrophobic material while a remainder of the fluid continues to pass across the hydrophobic material without adhering. This can allow the endospores present in the fluid under analysis to collect on the surface of the hydrophobic material, concentrating and isolating the endospores from the surrounding carrier fluid.

The hydrophobic collection material may be hydrophobic in that it does not bind or absorb water. For example, the hydrophobic collection material may repel polar molecules, such as water and molecules soluble in water, while allowing at least some types of non-polar molecules to bind to the surface of the material. The non-polar molecules may adhere to the surface of the hydrophobic material via hydrophobic attraction. Molecules having both polar and non-polar functional groups may or may not adhere to the hydrophobic material, e.g., depending on the hydrophobicity of the material being used, the length of the carbon chain separating a polar functional group from a non-polar functional group, and/or net polarity of the molecule.

When used, the hydrophobic collection material can capture and collect endospores out of a fluid passing over the material via hydrophobic attraction. As a fluid containing endospores passes across the hydrophobic collection material, the endospore may pass adjacent to and, in some examples, in contact with the surface of hydrophobic collection material. Since bacterial endospores present within the fluid may be non-polar and/or contain non-polar functional groups, the endospores can attract and attach to the surface of the hydrophobic material. These endospores can bind to the surface of the hydrophobic material via hydrophobic attraction forces, such as entropic interfacial forces. The magnitude of these forces may depend on the hydrophobicity of the interacting groups (e.g., the endospore and the hydrophobic material) as well as the distance separating them. In some examples, the hydrophobic forces increase approximately exponentially with decreasing separation distance.

The carrier fluid surrounding the endospores may continue to pass across the hydrophobic collection material without binding to the surface of the material. For example, when the carrier fluid is an aqueous fluid, the hydrophobic material can repel the polar water molecules present in the carrier fluid, causing the carrier fluid to flow past the hydrophobic material without attaching to the surface of the material. In this manner, the hydrophobic material can capture endospores out of the fluid sample passing across the material and collect the endospores on the surface material, generating an accumulated mass of endospores for subsequent analysis. In different examples, the fluid having passed across the hydrophobic material can be disposed or recycled and again passed across the hydrophobic material. For example, the fluid may be passed across the hydrophobic material two, three, or more times to increase the number of endospores collected out of the fluid by the hydrophobic material.

The volume of fluid passed across the hydrophobic material can vary, e.g., depending on the size of the hydrophobic material being used and the expected concentration of endospores in the sample under analysis. In some examples, the volume of fluid passed across the hydrophobic material is equal to or greater than the volume of the hydrophobic material itself. For example, the volume of fluid containing endospores that is passed across the hydrophobic material may be at least 10 times the volume of the hydrophobic material itself, such as at least 100 times the volume of the material, at least 1000 times the volume of the material or at least 10,000 times the volume of the material. In general, increasing the volume of fluid passed across the hydrophobic material increases the number of endospores captured on the surface of the material and available for analysis.

A fluid under analysis may be passed across the hydrophobic collection material (10) using a variety of different techniques. In some examples, the hydrophobic collection material is dipped or immersed into a reservoir containing the fluid under analysis and then pulled out of the reservoir to provide endospores hydrophobically-bound on the surface of the material and available for analysis. In other examples, a moving stream of fluid is flowed across the surface of the hydrophobic material, allowing endospores in the stream of fluid to attach to the surface of the material while a remainder of the fluid continues flowing past and away from the hydrophobic material. In such examples, the flow of fluid under analysis may be directed generally parallel to a planar surface of the hydrophobic material and/or generally transverse (e.g., perpendicular) to the planar surface of the hydrophobic material. For example, in some configurations described in greater detail with respect to FIG. 2, the hydrophobic material may be a porous material with pores sized to allow substantially all of the fluid under analysis to flow through the material. When so configured, the fluid under analysis may flow generally transverse to an external face of the hydrophobic material. Endospores may collect within the pores of the material while a remainder of the fluid continues flowing through the material and discharges on an opposite side of the hydrophobic material.

Independent of the specific configuration of the hydrophobic material utilized to collect bacterial endospores, the example technique of FIG. 1 includes optionally flushing the collected endospores with a flushing fluid (12). After passing the fluid to be evaluated across the hydrophobic material (10), the flow of fluid (in instance in which the fluid is flowed across the material) may be terminated to leave a hydrophobic material having collected endospores on its surface. This hydrophobic material may also contain residual fluid carrying the endospores, e.g., trapped between and around collected endospores on the surface of the collection material and/or within the pores of the material (in instances in which the material is porous). In some applications, this residual fluid may optically interfere with subsequent optical analysis of the endospores, if the fluid is not removed from the endospores before analysis. For example, the fluid carrying the endospores may emit fluorescent emissions when light within a wavelength ranging from 250 nanometers (nm) to 300 nm impinges upon the fluid. These emissions emitted by the carrier fluid may be within a wavelength ranging from 300 nm to 700 nm, which can overlap with a wavelength at which a lanthanide-dipicolinic acid complex fluoresces of, e.g., 450 nm to 650 nm. As a result, these emissions from the carrier fluid can obscure and/or distort emissions associated with the endospores, inhibiting accurate quantification of the endospores.

To help remove this contaminating fluid from the endospores, the endospores attached to the hydrophobic material may be flushed with a flushing fluid. The flushing fluid may be optically inert, e.g., such that residual flushing fluid remaining on the endospores does not interfere with subsequent optical analysis of the endospores. In one example, the flushing fluid is or includes liquid water (e.g., distilled water).

The hydrophobic material can be flushed, in different examples, by immersing the hydrophobic material containing the spores in a reservoir containing the flushing fluid and/or passing a moving stream of flushing fluid across the surface of the hydrophobic material and the endospores contained thereon. When the hydrophobic material is configured as a porous material, a pressurized stream of flushing fluid may be passed through the material (e.g., generally transversely), rinsing residual carrier fluid from around the endospores and from the pores of the material. In practice, some of the endospores captured on the surface of the hydrophobic material may be released into the flushing fluid. However, these lost endospores can be accounted for when calibrating the technique, e.g., by using a consistent amount of flushing fluid under consistent pressure conditions between a calibration run and subsequent operation.

When flushing is performed, the amount of flushing fluid passed over the collected endospores and/or through the hydrophobic material can vary, e.g., based on the concentration of the endospores in the sample under analysis and the optical interference impact of the carrier fluid. In some examples, the volume of flushing fluid passed across the hydrophobic material and the endospores collected thereon is at least equal to the volume of fluid under evaluation initially passed across the hydrophobic material. For example, if a volume of liquid containing endospores equal to "X" is passed across the hydrophobic collection material, the hydrophobic material may subsequently be flushed with a volume of flushing fluid greater than or equal to "X," such as a volume of flushing fluid greater than or equal to 1.5 times "X," greater than or equal to 2 times "X," or between "X" and 5 times "X." As one specific and non-limiting example, if 50 milliliters of fluid containing endospores was passed across the hydrophobic material, the material may subsequently be flushed with 100 milliliters of flushing fluid when using a flushing fluid ratio of 2 times "X." In some examples, a volume of flushing fluid sufficient to remove substantially all (and, in other examples, all) optically interfering carrier fluid from the endospores is used.

After capturing the bacterial endospores from the fluid under evaluation and optionally flushing the hydrophobic material containing captured endospores to remove optically interfering carrier fluid (12), the technique of FIG. 1 includes processing the endospores to release dipicolinic acid (14). Dipicolinic acid (DPA, 2,6-pyridinedicarboxylic acid) is typically present in high concentrations (e.g., approximately 1 molar percent or approximately 15% dry weight percent) in the core of endospores, typically as a 1:1 complex with $Ca^{2+}$. Dipicolinic acid is also a commercially available product having the following characteristics: CAS #: 499-83-2, Synonyms: 2,6 Pyridine Dicarboxylic Acid, Molecular Formula: C7H5NO4, Molecular Weight: 167.12, Description: White crystalline powder, Sulphated Ash: 0.3% max, Moisture Content: 0.5% max, Melting Point: 242.0 to 245.0.degree Celsius. Because dipicolinic acid is an indicator uniquely associated with bacterial endospores, the concentration of dipicolinic acid in a sample can be indicative of the number of endospores in the sample.

To detect and quantify the dipicolinic acid present in a sample according to the example technique of FIG. 1, the bacterial endospores collected on the surface(s) of the hydrophobic material can be processed in situ to release the dipicolinic acid from the cores of the spores. In some examples, a germination fluid is added to the endospores collected on the surface of the hydrophobic material, e.g., causing the endospores to transform to a vegetative cell and release dipicolinic acid. Germination involves the dormant endospore starting metabolic activity and thus breaking hibernation. It commonly includes rupture or absorption of the spore coat, swelling of the endospore, an increase in metabolic activity, and loss of resistance to environmental stress. The addition of the germination fluid, alone or in combination with heating, can initiate germination of the endospores.

In some examples, the technique of FIG. 1 includes adding a germination fluid to the hydrophobic material containing captured endospores to release dipicolinic acid (14). The germination fluid can be added to the endospores captured on the hydrophobic material, in different examples, by immersing the hydrophobic material containing the spores in a reservoir containing the germination fluid and/or passing a moving stream of germination fluid across the surface of the hydrophobic material and the endospores contained thereon. When the hydrophobic material is configured as a porous material, a pressurized stream of germination fluid may be passed through the material (e.g., generally transversely), exposing the endospores collected on the surface of the hydrophobic material (e.g., external surfaces and pore walls of the material) to germination fluid. Example germinating liquids that be used to release dipicolinic acid include, but are not limited to, L-alanine, L-asparagine, D-glucose, L-cysteine, dodecylamine, and the cocktail AGFK (containing D-glucose, D-fructose, KCl, and L-asparagine).

When used, the amount of germination fluid added to the hydrophobic material to initiate germination of the endospores captured on the material can vary. In some examples, the volume of germination fluid added to the hydrophobic material and the endospores collected thereon is less than the volume of fluid under evaluation initially passed across the hydrophobic material. For example, if a volume of liquid containing endospores equal to "X" is passed across the hydrophobic collection material, the amount of germination fluid subsequently added to the hydrophobic material and the endospores contained thereon may be less than "X," such as a volume of flushing fluid less than 0.5 times "X," less than 0.2 times "X," or less than 0.05 times "X." For example, the volume of germination fluid added to the hydrophobic material may range from 0.001 times "X" to 0.5 times "X," such as from 0.01 time "X" to 0.2 times "X," or from 0.025 times "X" to 0.1 times "X." As one specific and non-limiting example, if 50 milliliters of fluid containing endospores was passed across the hydrophobic material, 5 milliliters of germination fluid may then be added to the hydrophobic material (e.g., after optionally flushing the material with any of the previously mentioned volumes of flushing fluid) when using a germination fluid ratio of 0.1 times "X."

The germination fluid added to the hydrophobic material and endospores collected thereon may be captured and/or retained for subsequent optical analysis. By contrast, residual sample fluid passing over and/or through the hydrophobic material after depositing endospores and/or flushing fluid may be disposed after crossing the hydrophobic material. Accordingly, adding a smaller volume of germination fluid to the hydrophobic material can increase the concentration of endospores and/or dipicolinic acid in the germination fluid for subsequent analysis as compared to using a larger volume of germination fluid. This can be helpful when analyzing fluids having comparatively low concentrations of bacterial endospores.

In some examples, the germination fluid is heated prior to being added to the hydrophobic material and/or while the hydrophobic material containing endospores is immersed in the germination fluid. For example, the hydrophobic material containing captured endospores may be submerged in the germination fluid or the pore space of the hydrophobic material containing endospores may be saturated with germination fluid and then subject to heat shock. Heating the germination fluid can help initiate germination of the endospores and accelerate release of dipicolinic acid. In some examples, the germination material is heated to a temperature ranging from 75 degrees Celsius to 90 degrees Celsius, for example, for a time ranging from 15 minutes to 30 minutes.

In addition to or in lieu of adding a germination fluid to the bacterial endospores, the endospores may be destructively lysed by impacting the endospores with a core wall rupturing force. Example lysing methods include but are not limited to: microwaving, plasma cleaning, dry heating, autoclaving, sonicating and hydrogen chloride gassing. Lysing may destroy the core of the endospores, releasing dipicolinic acid.

The example technique of FIG. 1 also includes adding a lanthanide ion source to the dipicolinic acid released from the captured endospores to form a lanthanide-dipicolinic complex (16). Dipicolinic acid is a chemistry ligand that binds metal ions with high affinity. Once bound, the dipicolinic acid complex can emit an intense green fluorescence under UV excitation. The magnitude of this fluorescence can be correlated to the concentration of dipicolinic acid which, in turn, can be correlated with the number of endospores present in the sample under analysis.

A lanthanide ion source can be added to the dipicolinic acid released from the endospores captured on the hydrophobic material to form a fluorescing lanthanide-dipicolinic complex. Example lanthanide ions that can be added to the dipicolinic acid include, but are not limited to: terbium ($Tb^{3+}$), europium ($Eu^{3+}$), and dysprosium. In one example, terbium ($Tb^{3+}$) ions are used resulting in the formation of a terbium-dipicolinic acid complex. Typically, an excess amount of lanthanide ions are added to the dipicolinic acid that is sufficient to complex all dipicolinic acid molecules present in the sample.

To add lanthanide ions to the dipicolinic acid released from the endospores collected on the hydrophobic material, the lanthanide ions can be introduced to the germination fluid or other fluid (e.g., when destructive lysing in performed) that contains or will contain the dipicolinic acid. In one example, the lanthanide ions are added to the germination fluid prior to introducing the germination fluid to the endospores captured on the hydrophobic material. In such an application, the lanthanide ions can complex with the dipicolinic acid as the acid is being released from the endospores during germination. In another example, the lanthanide ions are added to the germination fluid after the endospores have germinated and released their dipicolinic acid, e.g., forming a germination fluid containing released dipicolinic acid. Therefore, although FIG. 1 illustrates the example technique as adding lanthanide ions (16) as a separate step after releasing dipicolinic acid from the captured endospores (14), it should be appreciated that the lanthanide ions may be present in the germination fluid such that the ions are added and combine with the dipicolinic acid as it is released from the endospores in a single step.

The technique of FIG. 1 also includes optically analyzing a fluid containing the lanthanide-dipicolinic acid complex and determining therefrom a concentration of bacterial endospores in the fluid under evaluation (18). The fluorescence of lanthanide ions is characterized by long lifetimes (e.g., 0.1 to 1 milliseconds), small extinction coefficients, and narrow emission bands. Narrow emission bands arise because the valence f-orbitals are shielded from the environment by the outer s and p electrons, and long lifetimes/small extinction coefficients arise because the transition between the emitting excited state and ground state is prevented. Thus, direct excitation of lanthanide ions leads to weak fluorescence due to the small absorption cross section. However, coordination of organic chromophores, like dipicolinic acid, with the lanthanide ions triggers intense lanthanide fluorescence. The dipicolinic acid serves as a light-harvesting center, and strong electronic coupling with downhill energetics allows the dipicolinic acid centered excitation energy to be efficiently transferred to the lanthanide ion, which subsequently fluoresces bright green.

In one example, the germination fluid or other fluid containing the lanthanide-dipicolinic acid complex is optically analyzed using a fluorometer. The fluorometer emits light into the fluid under analysis and, in response to receiving the emitted light, the lanthanide-dipicolinic complex emits fluorescent emissions. The fluorescent emissions may be at a different wavelength than the wavelength(s) of light emitted by the fluorometer into the fluid containing the lanthanide-dipicolinic acid complex. The fluorometer can detect the fluorescent emissions and determine the concentration of dipicolinic acid based on the optical response.

In another example, the germination fluid or other fluid containing the lanthanide-dipicolinic acid complex is optically analyzed using a spectrophotometer. The spectrophotometer emits light at one or more specific wavelength(s) into the fluid containing the lanthanide-dipicolinic acid complex and detects that amount of light passing through the fluid at those one or more wavelength(s). The amount of light absorbed by the fluid sample may be proportional to the concentration of the lanthanide-dipicolinic acid complex in the sample.

Independent of the technique used, the optical response of the fluid containing the lanthanide-dipicolinic acid complex may be proportional to the concentration of dipicolinic acid in the fluid. In turn, this dipicolinic acid is proportional to the concentration of endospores captured on the hydrophobic material, which is further correlated to the concentration of endospores in the original fluid sample under analysis. Accordingly, the optical response of the fluid containing the lanthanide-dipicolinic acid complex can be used with calibration data to determine the concentration of endospores in the original fluid sample under analysis.

FIG. 2 is a conceptual illustration of an example system 20 that can be used to determine the bacterial endospore count in a fluid according to the example technique of FIG. 1. System 20 can be implemented as an on-line monitoring station to continuously monitor the bacterial endospore count in a fluid being processed. Alternatively, system 20 can be implemented off-line, e.g., in a laboratory environment to periodically determine bacterial endospore counts in discrete fluid samples. System 20 is illustrated as including a source of aqueous liquid to be evaluated 22, an optional flushing fluid source 24, a germination fluid source 26, and a lanthanide ion source 28. System 20 also includes a hydrophobic material 30. Hydrophobic material 30 can receive aqueous liquid from liquid source 22, flushing fluid from source 24, germination fluid from source 26, and lanthanide ions from source 28. For example, hydrophobic material 30 and/or a housing containing the material may be fluidly connected to the different sources via fluid conduits conveying the fluids to the hydrophobic material. In other examples, hydrophobic material 30 and/or a housing containing the material may receive the fluids via manual transfer, e.g., performed by a laboratory technician.

In operation, hydrophobic material 30 can receive liquid from aqueous liquid source 22 and capture bacterial endospores out of the liquid. The bacterial endospores may hydrophobically bind and collect on the surfaces of the hydrophobic material 30 as the liquid flows over and/or through the material. As a result, the residual liquid having passed across hydrophobic material 30 may have a lower concentration of endospores (e.g., may be substantially devoid of endospores) than the liquid from source 22. This residual liquid having a reduced quantity of endospores can be disposed to drain 32 after passing across hydrophobic material 30 or recycled back across the material.

Hydrophobic material 30 may have endospores collected and held on its surface after terminating the flow of liquid from liquid source 22. If desired, hydrophobic material 30 can subsequently receive flushing liquid from flushing fluid source 24. The flushing liquid can flow across the surface of hydrophobic material 30 and over the endospores captured on the surface of the material, e.g., helping to remove optically interfering liquid from the endospores in preparation for subsequent optical analysis. The flushing liquid having passed across hydrophobic material 30 and containing residual carrier liquid (e.g., optically interfering liquid) can be disposed to drain 32. In other applications, hydrophobic material 30 is not flushed with a flushing liquid before optical analysis and, accordingly, system 20 does not include flushing fluid source 24.

After terminating the flow of flushing fluid from flushing fluid source 24 (when used), hydrophobic material 30 can receive germination fluid from germination fluid source 26. In one example, the germination fluid flows across the surface of hydrophobic material 30 and over the endospores captured on the surface of the material, e.g., collecting in a reservoir downstream of the hydrophobic material. In another example, the germination fluid is introduced into a housing containing hydrophobic material 30, resulting in the hydrophobic material and endospores collected thereon being partially or fully immersed in the germination fluid. This can allow the endospores captured by hydrophobic material 30 to germinate in situ, while being retained on the surface of the material. As discussed above with respect to FIG. 1, the endospores can release dipicolinic acid during germination, increasing the concentration of dipicolinic acid in the germination fluid (e.g., from an original concentration of zero).

To determine the concentration of dipicolinic acid in the germination fluid added to hydrophobic material 30 and, as a result, the concentration of endospores in aqueous liquid source 22, lanthanide ions are added to the dipicolinic-rich germination fluid from lanthanide ion source 28. In one example, the lanthanide ions are added to the dipicolinic-rich germination fluid while hydrophobic material 30 is partially or fully immersed in the germination fluid. In another example, the germination fluid is added to the dipicolinic-rich germination fluid after removing hydrophobic material 30, e.g., by discharging the fluid downstream of the material. In yet another example, the lanthanide ions are not added separately from germination fluid but instead are mixed with the germination fluid prior to being received by hydrophobic material 30 so as to provide a single source of both germination fluid and lanthanide ions. The lanthanide ions can combine with the dipicolinic acid released from the endospores to form an optically active lanthanide-dipicolinic acid complex.

System 20 in the example of FIG. 2 also includes an optical sensor 34 and a controller 36. Optical sensor 34 is configured to receive and optically analyze the germination fluid containing the lanthanide-dipicolinic acid complex generated from the endospores captured by hydrophobic material 30. Optical sensor 34 may include one or more optical emitters and one or more optical detectors. In operation, the one or more optical emitters direct light into fluid containing the lanthanide-dipicolinic acid complex and the one or more optical detectors detect fluorescent emissions generated by the fluid and, in particular, the lanthanide-dipicolinic acid complex contained within the fluid. The light directed into the fluid may generate fluorescent emissions by exciting electrons of the lanthanide-dipicolinic acid complex, causing the molecules to emit energy (i.e., fluoresce) that can be detected by the optical detectors. In some examples, the one or more optical emitters direct light at one frequency (e.g., ultraviolet frequency) into the fluid and cause the lanthanide-dipicolinic acid complex to emit light energy at a different frequency (e.g., visible light frequency, a different ultraviolet frequency).

Figure 2:
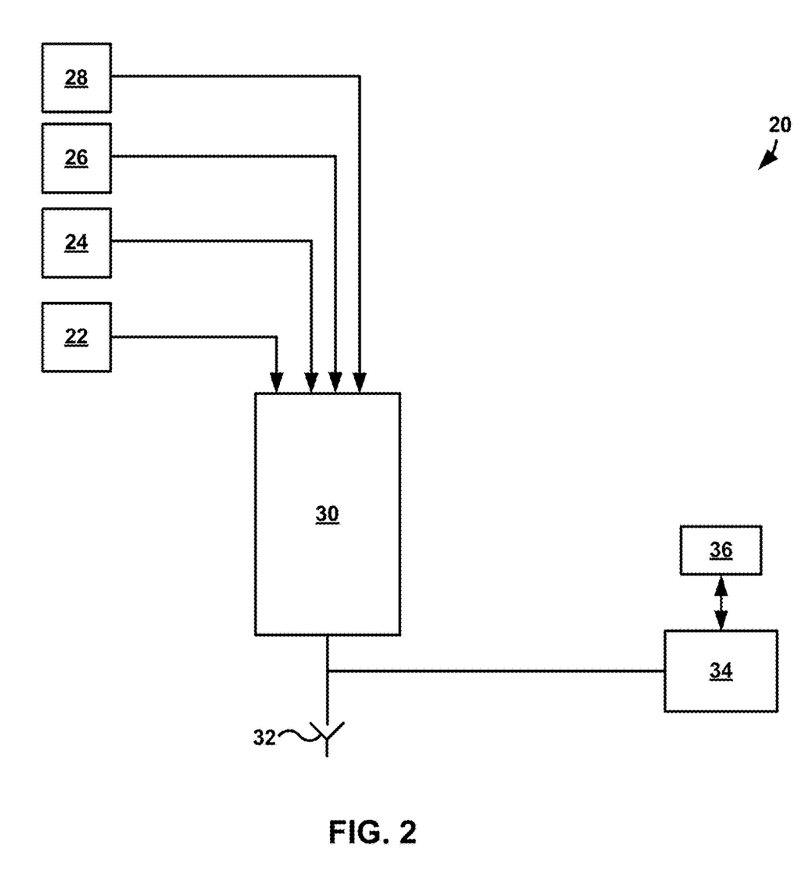
FIG. 2 is a conceptual illustration of an example system that can be used to determine the bacterial endospore count in a fluid according to the example technique of FIG. 1.

For example, optical sensor 34 may include one or more optical emitters that emit light within the ultraviolet (UV) spectrum, such as within wavelengths in the range from approximately 250 nm to approximately 300 nanometers. For example, the one or more optical emitters may emit within a wavelength from 270 nm to 280 nm. In response to this emitted light, the lanthanide-dipicolinic acid complexes within the fluid may generate fluorescent emissions at a wavelength from 450 nm to 650 nm. The one or more optical detectors of optical sensor 34 can detect the energy emitted by the fluorescing lanthanide-dipicolinic acid complexes at these wavelengths.

Controller 36 can control the one or more optical emitters to direct radiation into the fluid containing the lanthanide-dipicolinic acid complexes and also control the one or more detectors to detect fluorescent emissions emitted by the fluid. In some examples, controller 36 (or another controller within system 20) processes the light detection information to determine a concentration or count of endospores in the original aqueous liquid under analysis. For example, controller 36 can determine a concentration or count of the endospores in the aqueous liquid under analysis by comparing the magnitude of fluorescent emissions detected by the one or more optical detectors from a germination fluid prepared from a source liquid having an unknown concentration or count of endospores to the magnitude of the fluorescent emissions detected by the optical detectors from a germination fluid prepared having a known concentration or count of endospores. The unknown fluid may be prepared using the same or substantially same process as was used to prepare the calibration fluid. For example, the same volume of unknown source fluid may be passed across hydrophobic material 30 as was used to generate the calibration fluid, followed by use of the same volumes of flushing fluid, germination fluid, and lanthanide ion source. Calibration information can be stored in a non-transitory computer readable storage medium associated with controller 36.

In some examples, controller 36 manages the overall operation of system 20. Controller 36 may be communicatively coupled to various components within system 20, for example via a wired or wireless connection, so as to send and receive electronic control signals and information between controller 36 and the communicatively coupled components. For example, controller 36 may electronically actuate valves and/or control pumps within system 20 to control movements of the different fluids to and from hydrophobic material 30. Controller 36 can include a processor and memory. The memory may store software and data used or generated by controller. The memory may comprise a computer-readable medium, such as random access memory (RAM), read-only memory (ROM), non-volatile random access memory (NVRAM), electrically erasable programmable read-only memory (EEPROM), embedded dynamic random access memory (eDRAM), static random access memory (SRAM), flash memory, magnetic or optical data storage media. The memory may or may not be removable. The processor can run software stored in the memory to perform functions attributed to optical sensor 34 and controller 36 in this disclosure. The processor can include one or more processors, such as one or more microprocessors, digital signal processors (DSPs), application specific integrated circuits (ASICs), field programmable gate arrays (FPGAs), programmable logic circuitry, or the like, either alone or in any suitable combination.

As discussed above with respect to FIG. 1, hydrophobic material 30 can hydrophobically bind with endospores present in the fluid under analysis to concentrate and/or isolate the endospores from the remainder of the fluid. Hydrophobic material 30 can have a variety of different configurations and can function as a support surface on which endospores are captured and germinated. In some examples, hydrophobic material 30 is a non-porous (e.g., substantially non-porous) material. When so configured, fluid containing endospores can pass across the external surface(s) of the non-porous material and be collected on the enteral surface. In other examples, hydrophobic material 30 is a porous material having void spaces through which liquid can travel across the cross-section of the material. In these configurations, fluid containing endospores can pass across the external surface(s) of the hydrophobic material and/or internal surfaces of the material that bound and define the void spaces providing the material's porosity.

A porous hydrophobic material may be useful to increase the amount of surface area available for capturing endospores out of the fluid under analysis via hydrophobic attraction. In general, increasing the surface area of hydrophobic material 30 over which the fluid containing endospores passes increases the likelihood that endospores in the fluid will hydrophobically bond to the material and separate from the remaining fluid. The remainder of the fluid carrying the endospores, which may be composed of water and other polar molecules, can continue flowing through the pores or void spaces of the material and discharge on an opposite side of the material. In this way, the endospores can adhere to the wall surfaces bounding the various pores of hydrophobic material 30 while the remaining carrier fluid flows through the material, isolating and concentrating the endospores.

When hydrophobic material 30 is implemented using a porous material, the pores of the material may be sized large enough to allow substantially all (and, in other examples, all particles) in the fluid under analysis to flow through the pores of the material. For example, the pores of hydrophobic material 30 may be larger than the endospores being captured out of the fluid under analysis via hydrophobic attraction. In other words, instead of functioning as a filter that separates endospores via size exclusion, the pores of hydrophobic material 30 may be large enough to allow the endospores to pass through the hydrophobic material. The hydrophobic attraction forces between hydrophobic material 30 and the endospores may bind the endospores to the material and prevent the endospores from flowing out through the pores of the material, even though the endospores are smaller than the pores of the material. When so configured, hydrophobic material 30 may provide torturous (e.g., non-linear) fluid flow paths extending through the material and have a comparatively high surface area across which the fluid flows during endospore capture.

In some examples, hydrophobic material 30 has an average pore size greater than the average size of the bacterial endospores in the fluid under analysis, such as an average pore size at least 5 times larger than the average size of the bacterial endospores, at least 10 times larger, or at least 100 times larger, or at least 1000 times larger. In some additional examples, the distribution of pore sizes is such that at least 75% of the pores are at least 5 times larger (and in some examples at least 10 times larger) than the average size of the bacterial endospores in the fluid under analysis, such as at least 90% of the pores, at least 95% of the pores, or at least 99% of the pores.

The size of the pores of hydrophobic material 30 can also vary depending on the size of particles other than the endospores within the fluid under analysis, which will depend on the composition of the fluid under analysis. In the case of milk, for example, milk may contain protein micelles having a size of approximately 0.1 micrometers, fat globules ranging from 0.2 micrometers to 15 micrometers, endospores ranging from 0.6 micrometers to 1 micrometer, bacteria ranging from 1 micrometer to 5 micrometers, and somatic cells ranging from 10 micrometers to 15 micrometers, among other particles. Hydrophobic material 30 may have pores sized larger than substantially all particles in the fluid in an attempt to allow the non-endospore particles to flow through the material without blocking the pores. In some examples, hydrophobic material 30 has an average pore size greater than the average size of the particles in the fluid under analysis, such as an average pore size at least 5 times larger than the average size of the smallest particles (e.g., class of particles) in the fluid, at least 10 times larger, or at least 100 times larger, or at least 1000 times larger. In some additional examples, the distribution of pore sizes is such that at least 75% of the pores are at least 5 times larger (and in some examples at least 10 times larger) than the average size of the smallest particles in the fluid under analysis, such as at least 90% of the pores, at least 95% of the pores, or at least 99% of the pores. In one example, at least 95% of the pores range from 10 times larger to 1000 times larger than the smallest sized class of particles in the fluid under analysis.

While the absolute size of the pores of hydrophobic material 30 can vary based on the desired application, in some examples, the hydrophobic material has an average pore size greater than 25 micrometers, such as greater than 50 micrometers, greater than 100 micrometers, or greater than 125 micrometers. In some examples, the hydrophobic material has a porosity ranging from 20 percent of the total volume of the hydrophobic material to 70 percent of the total volume of the material.

Hydrophobic material 30 can capture and collect endospores out of a fluid passing over the material via hydrophobic attraction. Accordingly, hydrophobic material 30 can exhibit a sufficient hydrophobicity to selectively bind with endospores in the fluid under analysis while allowing the surrounding fluid carrying the endospores to pass across the hydrophobic material without binding. In some examples, hydrophobic material 30 is sufficiently hydrophobic such that substantially all endospores present in the fluid under analysis bind to the hydrophobic material while passing across the material. In different configurations, hydrophobic material 30 may capture greater than 30% of the endospores present in the fluid under analysis on the surface of the material, such as greater than 50% of the endospores, greater than 70% of the endospores, greater than 90% of the endospores, or greater than 95% of the endospores. The resulting fluid having passed across hydrophobic material 30 may contain less than 50% of the endospores present in the original fluid initially contacting the material, such as less than 40% of the endospores, less than 30% of the endospores, or less than 10% of the endospores. The percentage of endospores captured by the hydrophobic material may be modified by adjusting the hydrophobicity of the material and/or the amount of hydrophobic material the fluid encounters.

Because hydrophobic materials repel water, the hydrophobicity of a material can be characterized by the contact angle between a water droplet placed on the material and the surface of the material. For example, the water contact angle of hydrophobic material 30 can be determined by placing a droplet of water on the surface of the material and taking measurements of the drop and/or measuring the wetting angle that forms at the liquid-surface interface. One standard method used to measure the water contact angle is by measuring the maximum height and width of a sessile drop. Based on a ratio of the drop height to the drop width, the contact angle between the drop and the surface is calculated according to known equations. In some examples, hydrophobic material 30 exhibits a contact angle with water greater than 80 degrees, such as a contact angle greater than 90 degrees.

Hydrophobic material 30 can be constructed from a variety of different materials. Example materials that can be used to fabricate hydrophobic material 30 include, but are not limited to, polyethylene, polypropylene, polyvinylchloride, polyamide, polystyrene, polytetrafluoroethylene (e.g., Teflon®), ethylene propylene diene (EPDM), nitrile rubber (e.g., Buna-N), polyethylene terephthalate, aliphatic polyamides (e.g., Nylon), aramid fabric (e.g., Kevlar®), and stainless steel. For example, hydrophobic material 30 may be formed from a sintered metal powder or porous plastic. Hydrophobic material 30 may or may not be surface treated to increase the hydrophobicity of the material.

Hydrophobic material 30 can have any desired size and shape. Typically, the size of hydrophobic material 30 will vary based on the amount of fluid intended to be analyzed, with larger volumes of fluid using larger volumes of hydrophobic material. Hydrophobic material 30 can be implemented as a planar sheet of material (e.g., a disc), a sphere of material, a cylinder of material (e.g., an annulus), or any other desired shape. In some examples, hydrophobic material 30 is implemented as a single structure (e.g., sheet) that fluid containing endospores passes over and/or through. In other examples, a plurality of hydrophobic structures may be used in close proximity, e.g., to provide a packed bed, column, or cartridge of hydrophobic material that fluid containing endospores flows through.

In general, the foregoing examples describe the use of a hydrophobic material to concentrate and/or isolate bacterial endospores from a fluid sample followed by germination and optical analysis to determine the concentration or count of endospores in the fluid sample. Hydrophobic materials described as being suitable for capturing and collecting endospores out of a fluid may be used in other applications beyond quantifying the endospores via optical analysis. For example, the hydrophobic materials can be used in a manufacturing facility to purify a fluid containing endospores by passing the fluid across the hydrophobic material. The hydrophobic material can capture the endospores in the fluid and purify the fluid for downstream processing or sale. For example, the hydrophobic material may remove greater than 80% of the endospores present in the fluid, such as greater than 90% of the endospores, or greater than 99% of the endospores. In such applications, the hydrophobic material may be periodically flushed to remove captured endospores and to reopen surface area for endospore bonding. In still other examples, the hydrophobic material may be used in a laboratory setting to concentrate and/or isolate bacterial endospores from a fluid sample without subsequently germinating and/or optically analyzing the captured endospores. Rather, the concentrated and/or isolated endospores can be used to perform other types of laboratory analyses.

Further, although the foregoing examples describe the use of a hydrophobic material to capture and collect endospores out of a fluid passing over the material via hydrophobic attraction, in other examples, endospores can be isolated from a fluid sample without relying on hydrophobic attraction forces. For example, a mechanical filter may be used to separate endospores from a surrounding fluid based on size exclusion. In these examples, the mechanical filter may or may not be fabricated from a hydrophobic material.

The following examples may provide additional details about systems and techniques in accordance with this disclosure.

EXAMPLE 1

A variety of milk solutions containing different bacterial endospores counts were passed across a hydrophobic material having a porosity of approximately 50 percent (e.g., ranging from 25% void space to 75% void space). Fifty milliliters of milk were passed across the hydrophobic material followed by two successive flushes of 50 milliliters each of water. Subsequently, 2 milliliters of L-alanine (10 mM) type germination fluid were added to the hydrophobic material and heated at a temperature of 75 degrees Celsius for 15 minutes. A terbium reagent was then added to the germinate fluid to form a terbium-dipicolinic acid complex. The germinate fluid containing the terbium-dipicolinic acid complex was fluorometrically analyzed by emitting light into the fluid samples and generating and detecting fluorescent emissions from the fluids.

Figure 3:
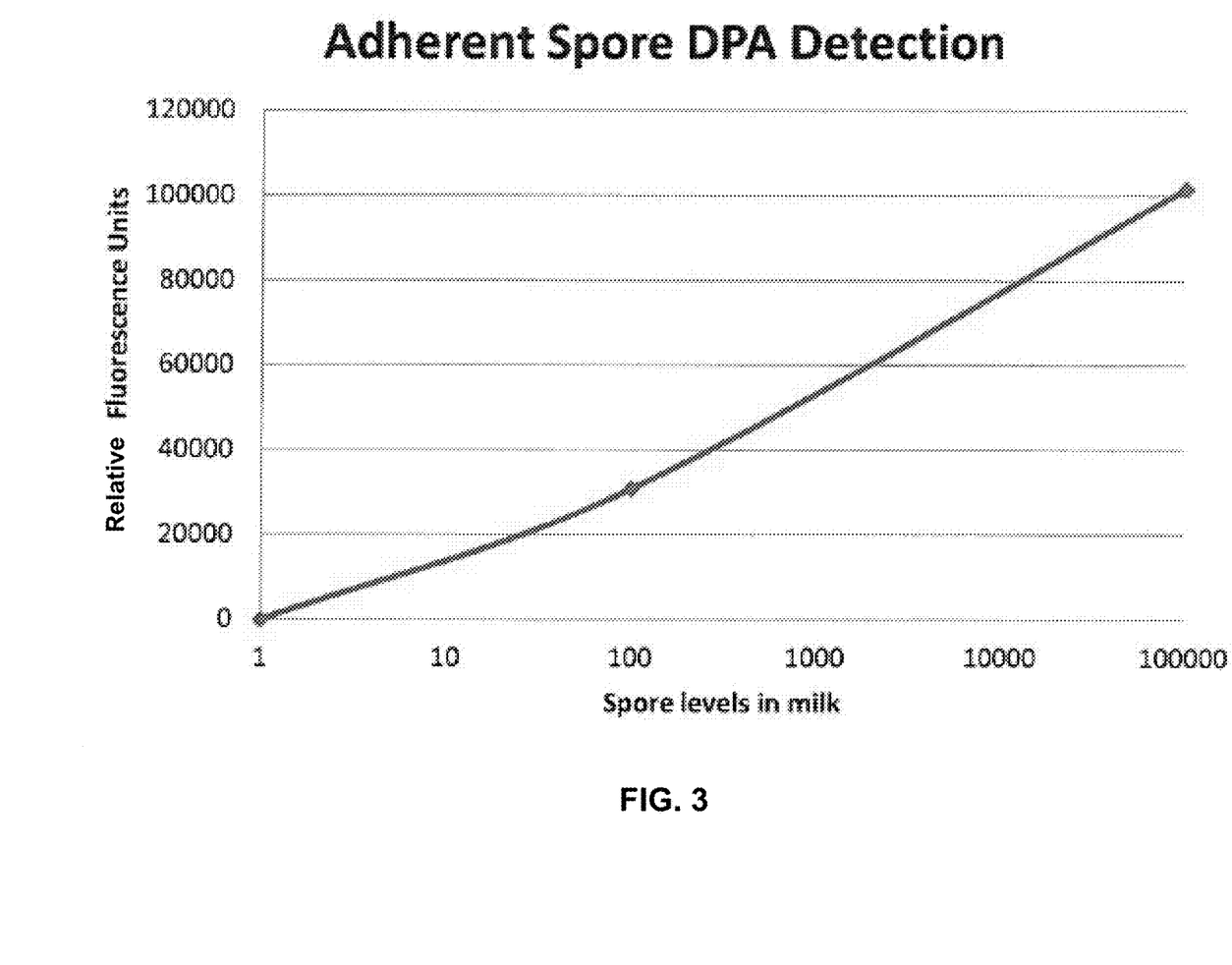
FIG. 3 is a plot showing example optical responses of fluids prepared by passing milk samples across a hydrophobic material.

FIG. 3 is a plot showing the optical response of the example milk samples. The X-axis of the plot is the endospore level in the milk samples in counts. The Y-axis is the optical response of the germinant fluid containing terbium-dipicolinic acid complex that was generated from the milk samples, in relative fluorescence units.

EXAMPLE 2

Figure 4:
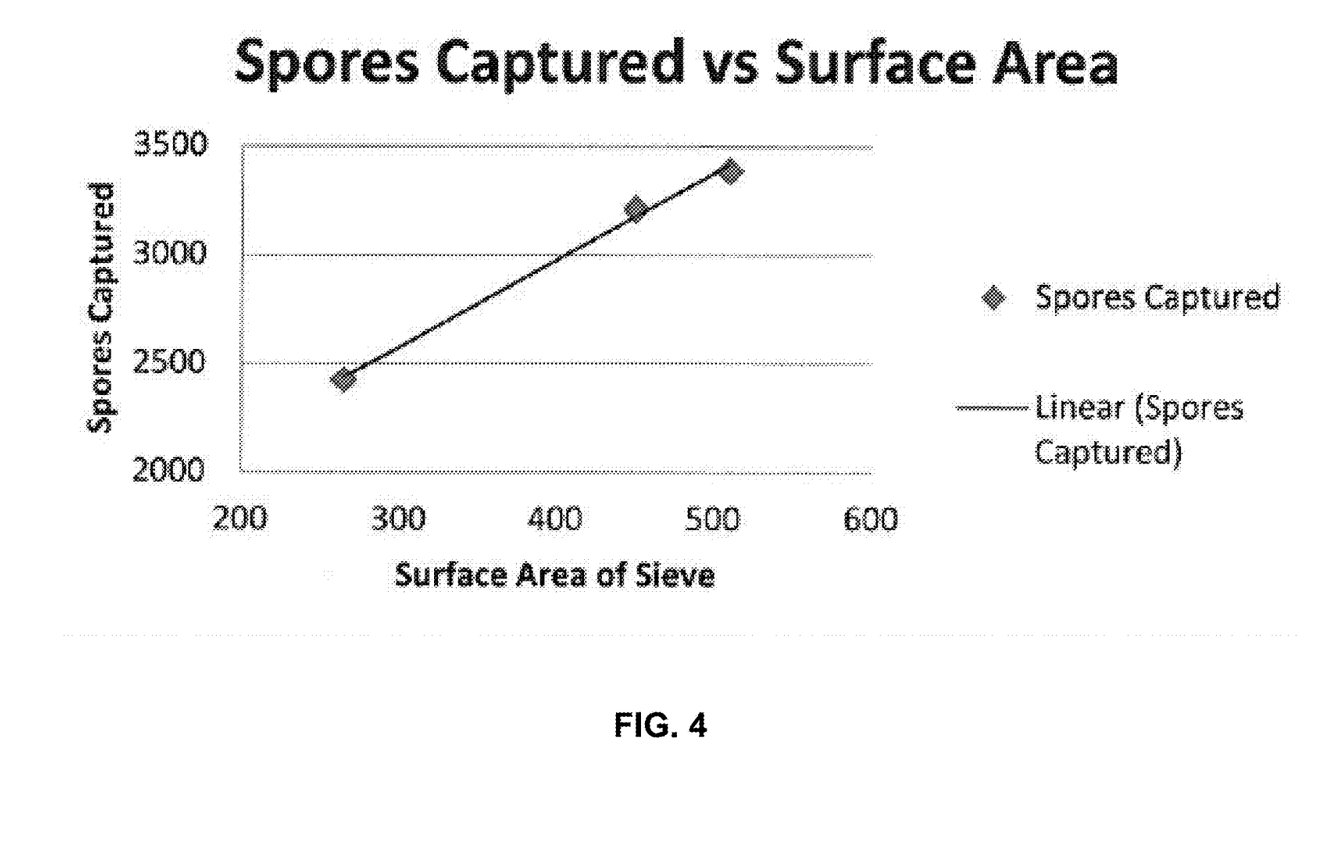
FIG. 4 is a plot showing an example number of endospores captured versus surface area of an example hydrophobic material.

To evaluate the effect of hydrophobic material pore size on endospore capture, hydrophobic materials were fabricated having different average pore sizes, including one having an average pore size of 65 micrometers and one having an average pore size of 125 micrometers. Subsequently, 50 milliliters of milk having an endospore count of $1 \times 10^2$ was passed through each hydrophobic collection material. The endospores were believed to have ranged in size from approximately 0.7 micrometers to approximately 1 micrometer. The residual milk discharged from the hydrophobic collection material was recycled back through the material such that the milk passed through hydrophobic material three times. FIG. 4 is a plot showing the number of endospores captured following the process versus the surface area of the hydrophobic material. The larger surface areas correspond to the hydrophobic materials having the small average pore sizes. The testing showed the hydrophobic material captured from about 50% of the spores to about 70% of the spores following the third pass of the milk.

Figure 5:
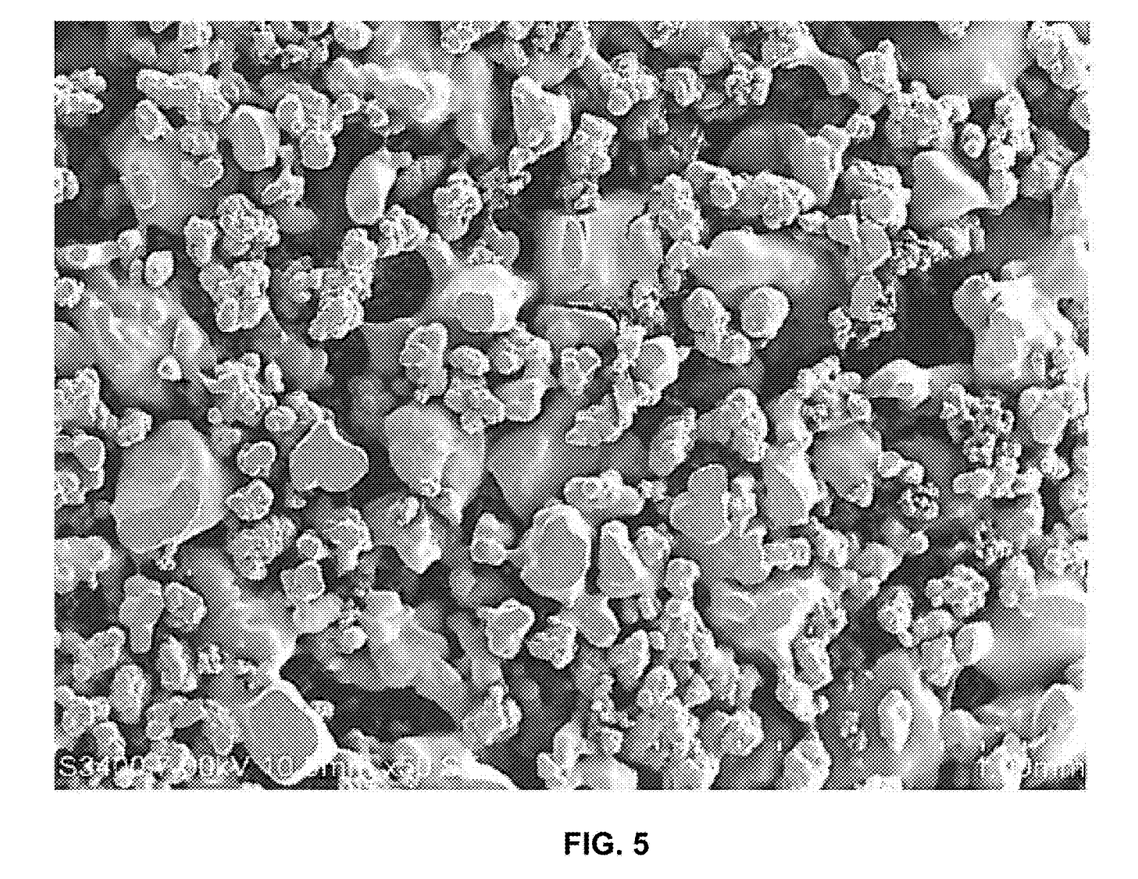
FIG. 5 is a micrograph showing one example hydrophobic material at a resolution of 1 millimeter after passing milk through the material.
Figure 6:
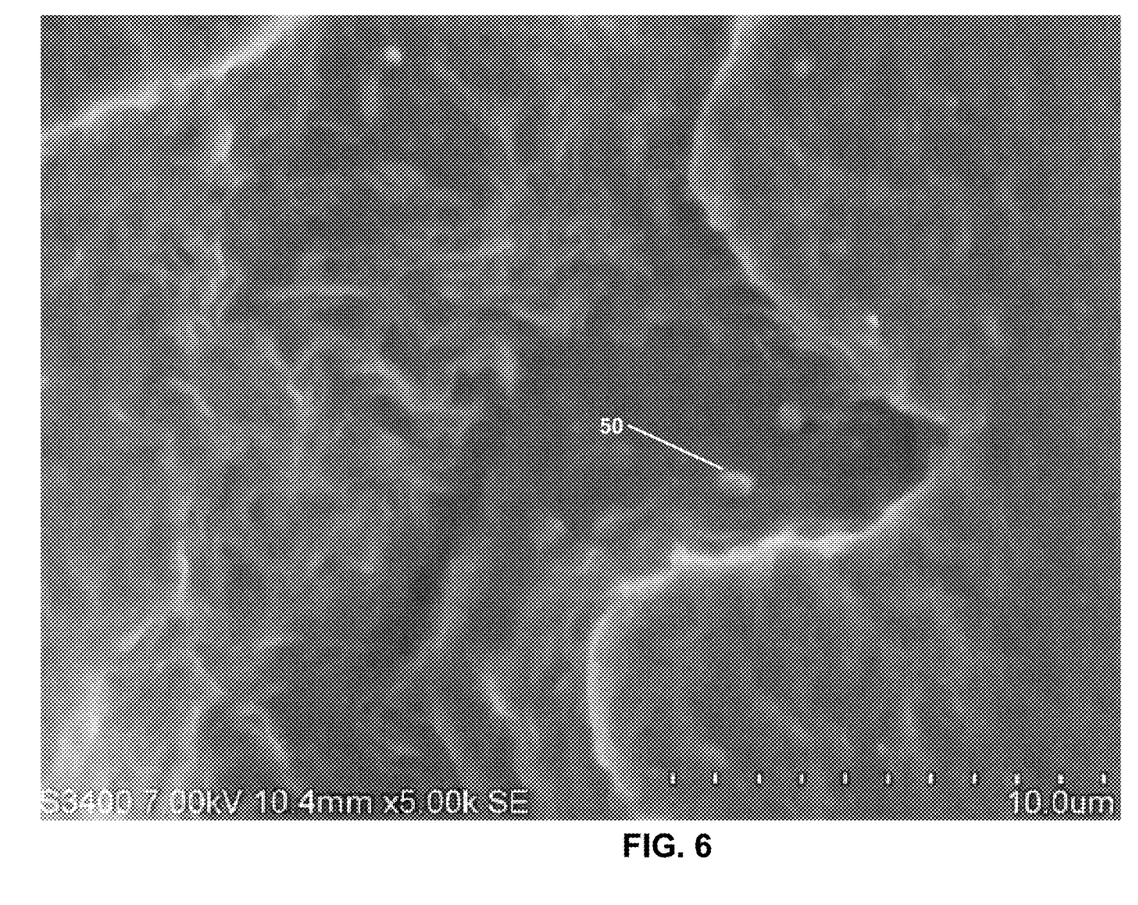
FIG. 6 is a 100 time magnification of the micrograph of FIG. 5 showing endospores adhered to the surface of the material.

FIG. 5 is a micrograph of one of the hydrophobic materials at a resolution of 1 millimeter after passing the milk through the material three times. The figure shows the overall structure of the material and the relative size of an example pore structure. FIG. 6 is a 100 time magnification of the micrograph of FIG. 5 showing an endospore 50 adhered to the surface of material. The images indicate the endospores were captured via hydrophobic attraction and not mechanical size exclusion (e.g., filtering).

In the example, the hydrophobic materials were subsequently flushed with 50 milliliters of water. Testing showed that greater than from approximately 99% to approximately 99.9% of the endospores remained adhered to the surface of the hydrophobic material after flushing.

The invention claimed is:

1. A method comprising:
    passing an aqueous liquid containing bacterial endospores across a hydrophobic collection material comprising a porous material having an average pore size greater than an average size of the bacterial endospores and collecting bacterial endospores on the hydrophobic collection material via hydrophobic attraction, wherein the aqueous liquid containing the bacterial endospores emits fluorescence at a wavelength overlapping with a wavelength at which a lanthanide-dipicolinic acid complex fluoresces;
    flushing the collected bacterial endospores to remove residual aqueous liquid from the collected bacterial endospores that fluoresces at the wavelength overlapping with the wavelength at which a lanthanide-dipicolinic acid complex fluoresces;
    subsequent to flushing the collected bacterial endospores, releasing dipicolinic acid (DPA) from the collected bacterial endospores;
    adding a lanthanide source to the dipicolinic acid released from the collected bacterial endospores to form a lanthanide-dipicolinic acid complex; and
    determining a concentration of the bacterial endospores in the aqueous liquid based on an optical response of the lanthanide-dipicolinic acid complex.

2. The method of claim 1, wherein the average pore size of the hydrophobic collection material is at least 5 times larger than the average size of the bacterial endospores.

3. The method of claim 2, wherein passing the aqueous liquid containing bacterial endospores across the hydrophobic collection material comprises passing the aqueous liquid containing bacterial endospores through the porous material such that bacterial endospores collect on the porous material while substantially all remaining aqueous liquid passes through the porous material.

4. The method of claim 1, wherein the hydrophobic collection material comprises a porous material having a porosity ranging from 20 percent of a total volume of the hydrophobic collection material to 70 percent of the total volume of the hydrophobic collection material.

5. The method of claim 1, wherein the hydrophobic collection material exhibits a contact angle with water greater than 90 degrees.

6. The method of claim 1, wherein the hydrophobic collection material comprises at least one polyethylene, polypropylene, polyvinylchloride, polyamide, polystyrene, polytetrafluoroethylene, and stainless steel.

7. The method of claim 1, wherein flushing the collected bacterial endospores comprises flushing the collected bacterial endospores with at least one and a half times a volume of the aqueous liquid containing bacterial endospores passed across the hydrophobic collection material.

8. The method of claim 1, wherein releasing dipicolinic acid (DPA) from the collected bacterial endospores comprises adding a germination fluid to the collected bacterial endospores.

9. The method of claim 8, wherein adding the germination fluid to the collected bacterial endospores comprises adding a volume of germination fluid less than one fifth a volume of the aqueous liquid containing bacterial endospores passed across the hydrophobic collection material.

10. The method of claim 8, wherein the lanthanide source comprises terbium and adding the lanthanide source to the dipicolinic acid released from the collected bacterial endospores comprises adding terbium to the germination fluid such that the lanthanide-dipicolinic acid complex comprises a terbium-dipicolinic acid complex.

11. The method of claim 10, wherein determining the concentration of the bacterial endospores in the aqueous liquid based on the optical response of the lanthanide-dipicolinic acid complex comprises directing light into the germination fluid containing the terbium-dipicolinic acid complex and thereby generating fluorescent emissions from the terbium-dipicolinic acid complex and detecting the fluorescent emissions emitted by the terbium-dipicolinic acid complex.

12. The method of claim 1, wherein the aqueous liquid is a dairy product.

13. The method of claim 1, wherein the bacterial endospores comprise at least one of *Bacillus subtilis, Bacillus cereus, Bacillus amyloliquefaciens, Bacillus atrophaeus, Bacillus megaterium, Bacillus coagulans, Bacillus pumilus, Bacillus mycoides, Bacillus licheniformis, Bacillus sporothermodurans, Bacillus thuringensis, Bacillus weihenstephanensis, Geobacillus stearothermophilus,Clostridium tyrobutyricum, Alicyclobacillus, Clostridium botulinum, Clostridium difficile,* and *Bacillus anthracis.*

14. The method of claim 1, wherein the aqueous liquid emits fluorescence within a wavelength ranging from 300 nm to 700 nm, and the lanthanide-dipicolinic acid complex fluoresces at a wavelength ranging from 450 nm to 650 nm.

15. The method of claim 1, wherein the aqueous liquid emits fluorescence within a wavelength ranging from 300 nm to 700 nm, and the lanthanide-dipicolinic acid complex fluoresces at a wavelength ranging from 450 nm to 650 nm.

16. The method of claim 1, wherein passing the aqueous liquid containing bacterial endospores across the hydrophobic collection material and thereby collecting bacterial endospores comprises hydrophobically binding the endospores to the hydrophobic collection material while allowing the aqueous liquid surrounding the bacterial endospores to pass across the hydrophobic collection material without binding to the hydrophobic collection material.

17. The method of claim 1, wherein the aqueous liquid is milk.

18. The method of claim 17, wherein
the milk comprises protein micelles having a size of approximately 0.1 micrometers, fat globules having a size ranging from 0.2 micrometers to 15 micrometers, the bacterial endospores having the average size ranging from 0.6 micrometers to 1 micrometer, bacteria having a size ranging from 1 micrometer to 5 micrometers, and somatic cells having a size ranging from 10 micrometers to 15 micrometers, and
the average pore size is greater than the size of the protein micelles, the size of the fat globules, the average size of the bacterial endospores, the size of the bacteria, and the size of the somatic cells.

19. The method of claim 1, wherein the average pore size is greater than 25 micrometers.

20. The method of claim 1, wherein the hydrophobic collection material defines tortuous fluid flow paths extending through the hydrophobic collection material, and passing the aqueous liquid containing bacterial endospores across the hydrophobic collection material comprises passing aqueous liquid containing bacterial endospores through the tortuous fluid flow paths.

21. The method of claim 1, wherein the average pore size of the hydrophobic collection material is at least 100 times larger than the average size of the bacterial endospores.

22. The method of claim 1, wherein at least 95% of the pores of the porous hydrophobic collection material are at least 5 times larger than the average size of the bacterial endospores.

23. A method comprising:
passing an aqueous liquid comprising bacterial endospores through a porous hydrophobic collector having an average pore size greater than an average size of the bacterial endospores and thereby capturing bacterial endospores present in the aqueous liquid on a surface of the porous hydrophobic collector via hydrophobic attraction between the porous hydrophobic collector and the bacterial endospores, wherein the aqueous liquid comprising the bacterial endospores emits fluoresce at a wavelength overlapping with a wavelength at which a lanthanide-dipicolinic acid complex fluoresces;
flushing the porous hydrophobic collector with an optically inert liquid to remove residual aqueous liquid from the bacterial endospores captured on the porous hydrophobic collector that fluoresces at the wavelength overlapping with the wavelength at which a lanthanide-dipicolinic acid complex fluoresces;
subsequent to flushing the porous hydrophobic collector, adding a germination fluid to the porous hydrophobic collector so as to release dipicolinic acid (DPA) from bacterial endospores captured on the porous hydrophobic collector;
providing a lanthanide source to form a lanthanide-dipicolinic acid complex in the germination fluid with the dipicolinic acid released from the bacterial endospores captured on the porous hydrophobic collector; and
fluorometrically analyzing the germination fluid to determine a concentration of bacterial endospores in the aqueous liquid.

24. The method of claim 23, wherein passing the aqueous liquid through the porous hydrophobic collector comprises passing a volume X through the porous hydrophobic collector, flushing the porous hydrophobic collector comprises flushing the porous hydrophobic collector with a volume of optically inert liquid ranging at least 1.5 times X, and adding the germination fluid to the porous hydrophobic collector comprises adding a volume of germination fluid ranging from 0.01 to 0.2 times X.

25. The method of claim 23, wherein the average pore size of the porous hydrophobic collector is at least 5 times larger than the average size of the bacterial endospores.

26. The method of claim 23, wherein the porous hydrophobic collector has a porosity ranging from 20 percent of a total volume of the porous hydrophobic collector to 70 percent of the total volume of the porous hydrophobic collector, and the porous hydrophobic collector comprises at least one polyethylene, polypropylene, polyvinylchloride, polyamide, polystyrene, polytetrafluoroethylene, and stainless steel.

27. The method of claim 23, wherein the lanthanide source comprises terbium and bacterial endospores comprise at least one of *Bacillus subtilis, Bacillus cereus, Bacillus amyloliquefaciens, Bacillus atrophaeus, Bacillus megaterium, Bacillus coagulans, Bacillus pumilus, Bacillus mycoides, Bacillus licheniformis, Bacillus sporothermodurans, Bacillus thuringensis,Bacillus weihenstephanensis, Geobacillus stearothermophilus,Clostridium tyrobutyricum, Alicyclobacillus, Clostridium botulinum, Clostridium difficile,* and *Bacillus anthracis.*

28. The method of claim 23, wherein the aqueous liquid is a human-consumable food or beverage.

29. The method of claim 23, wherein the aqueous liquid is milk comprising protein micelles having a size of approximately 0.1 micrometers, fat globules having a size ranging from 0.2 micrometers to 15 micrometers, the bacterial endospores having the average size ranging from 0.6 micrometers to 1 micrometer, bacteria having a size ranging from 1 micrometer to 5 micrometers, and somatic cells having a size ranging from 10 micrometers to 15 micrometers, and the average pore size is greater than the size of the protein micelles, the size of the fat globules, the average size of the bacterial endospores, the size of the bacteria, and the size of the somatic cells.

30. The method of claim 23, wherein the porous hydrophobic collector has tortuous fluid flow paths defining pores of the porous hydrophobic collector, and passing the aqueous liquid comprising bacterial endospores across the porous hydrophobic collector comprises passing aqueous liquid comprising bacterial endospores through the tortuous fluid flow paths.

31. The method of claim 23, wherein the average pore size is greater than 25 micrometers.

* * * * *

UNITED STATES PATENT AND TRADEMARK OFFICE
CERTIFICATE OF CORRECTION

PATENT NO. : 10,316,347 B2  
APPLICATION NO. : 14/315606  
DATED : June 11, 2019  
INVENTOR(S) : Anthony Wayne Erickson et al.

Page 1 of 1

It is certified that error appears in the above-identified patent and that said Letters Patent is hereby corrected as shown below:

On the Title Page

Column 2, Other Publications, Line 18, Delete "Disseration" and insert -- Dissertation --

In the Claims

Column 19, Line 21, Claim 13, delete "thuringensis," and insert -- thuringiensis --

Column 19, Line 22, Claim 13, delete "stearothermophilus,Clostridium" and insert -- stearothermophilus, Clostridium --

Column 20, Line 62, Claim 27, delete "thuringensis,Bacillus" and insert -- thuringiensis, Bacillus --

Column 20, Line 63, Claim 27, delete "stearothermophilus,Clostridium" and insert -- stearothermophilus, Clostridium --

Signed and Sealed this  
Tenth Day of September, 2019

Andrei Iancu  
*Director of the United States Patent and Trademark Office*